United States Patent [19]

Jäger et al.

[11] 3,931,171

[45] Jan. 6, 1976

[54] PROCESS FOR THE PRODUCTION OF 2,3-DIHYDRO-1,3-OXAZINEDIONE-(2,4)-COMPOUNDS

[75] Inventors: Gerhard Jäger, Wuppertal-Elberfeld; Hans-Jurgen Weinzelburger, Wuppertal-Cronenberg; Richard Wegler, Leverkusen, all of Germany

[73] Assignee: Bayer Aktiengesellschaft, Leverkusen, Germany

[22] Filed: Nov. 13, 1972

[21] Appl. No.: 306,125

Related U.S. Application Data

[63] Continuation of Ser. No. 109,951, Jan. 26, 1971, abandoned.

[30] Foreign Application Priority Data

Feb. 5, 1970   Germany............................ 2005118

[52] U.S. Cl........... 260/244 R; 260/260; 260/340.2; 260/586 R; 260/592; 260/593 R; 260/599; 260/601 R
[51] Int. Cl.².............. C07D 265/08; C07D 265/12
[58] Field of Search............................ 260/244, 260

[56] References Cited
UNITED STATES PATENTS

| | | | |
|---|---|---|---|
| 2,336,868 | 12/1943 | Jayne et al. | 260/564 E |
| 2,758,994 | 8/1956 | Lacey | 260/260 |
| 2,849,306 | 8/1958 | Searle | 260/564 E |
| 3,190,795 | 6/1965 | Hensley et al. | 260/564 E |
| 3,235,360 | 2/1966 | Soboczenski | 260/260 |
| 3,235,361 | 2/1966 | Loux | 260/260 |
| 3,480,631 | 11/1969 | Cummins | 260/260 |
| 3,654,362 | 4/1972 | Brokke et al. | 260/564 E |
| 3,717,633 | 2/1973 | Stahle et al. | 260/564 E |

*Primary Examiner*—Harry I. Moatz
*Attorney, Agent, or Firm*—Burgess, Dinklage & Sprung

[57] ABSTRACT

2,3-dihydro-1,3-oxazinediones-(2,4) are produced in one step with good yields and at low reaction times by reacting a corresponding 1,3-dioxinone-(4) with an appropriate isocyanate at temperatures of e.g., 80° to 200°C.

Certain novel oxazinediones, useful as intermediates for making herbicides, are produced thereby.

17 Claims, No Drawings

PROCESS FOR THE PRODUCTION OF 2,3-DIHYDRO-1,3-OXAZINEDIONE-(2,4)-COMPOUNDS

This is a continuation of application Ser. No. 109,951, filed Jan. 26, 1971, now abandoned.

The present invention relates to a process for the preparation of 2,3-dihydro-1,3-oxazinedione-(2,4) compounds and to certain novel compounds produced thereby.

It is known that 2,3-dihydro-6-methyl-1,3-oxazinediones-(2,4) substituted in 3-position are obtained when symmetrically N,N'-disubstituted S-methylisothioureas are reacted with diketene in boiling benzene and the 3-substituted 2-alkyl- or 2-arylimino-2,3-dihydro-6-methyl-1,3-oxazinones-(4) formed are heated with aqueous hydrochloric acid (J. Chem. Soc. 1954, 845).

Furthermore, it is known that 3-phenyl- or 3[α-naphthyl]-5,6-trimethylene-2,3-dihydro-1,3-oxazinedione-(2,4) is formed in respective yields of 25% (phenyl compound) or 5% (naphthyl compound) of the theoretical when 2-bromocyclohexanedione-(1,3) is reacted with, respectively, phenyl- or α-naphthylisocyanate in benzene in the presence of equivalent amounts of triethylamine (Tetrahedron Letters 1967, 2089 – 2092).

Inherent in the known processes, however, are a number of disadvantages. Thus, the S-methylisothiourea method is restricted to the use of symmetrically N,N'-disubstituted S-methylisothioureas as starting materials and to the preparation of 3-substituted 2,3-dihydro-6-methyl-1,3-oxazinediones-(2,4). Moreover, in the known two-step process the isolation of the intermediate product is necessary. The 2-bromocyclohexanedione method gives the 5,6-trimethylene-2,3-dihydro-1,3-oxazinediones-(2,4) in only slight yields.

The present invention provides a process for the production of a 2,3-dihydro-1,3-oxazinedione-(2,4) of the general formula

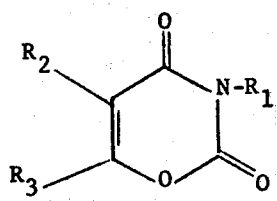
(I)

in which $R_1$ is alkyl, haloalkyl, cycloalkyl, norbornylalkyl, aralkyl, acyl or arylsulfonyl or aryl which radicals may be substituted by one or more alkyl, alkenyl, aryl, alkoxy, alkylmercapto, alkylsulfoxyl, alkylsulfonyl, haloalkyl, fluorine, chlorine, bromine, iodine, cyano, nitro, amino, alkylamino, dialkylamino or heterocyclic groups; or $R_1$ can be a heterocyclic radical; or $R_1$ can be the group of the formula

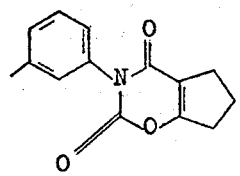

$R_2$ is hydrogen and $R_3$ is methyl, or $R_2$ and $R_3$ together form a trimethylene radical which may be substituted by one or more alkyl radicals.

The instant process comprises reacting a 1,3-dioxinone(4) of the general formula

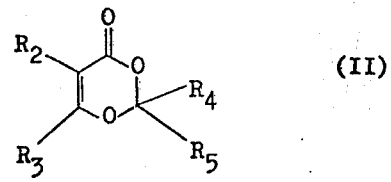
(II)

in which $R_2$ and $R_3$ have the meaning stated above, and
$R_4$ is hydrogen or alkyl, and
$R_5$ is alkyl or aryl, or
$R_4$ and $R_5$ taken together form a divalent alkylene group of the formula $-(CH_2)_n-$, where $n$ is 4, 5 or 6;

with an isocycanate of the general formula $$R_1'-N=C=O \qquad (III)$$

in which $R_1'$ has the meaning stated above for $R_1$, except that $R_1'$ cannot be the group of the formula

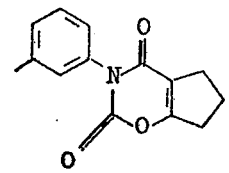

but $R_1'$ may also be a radical of the formula

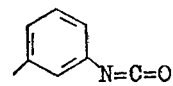

Preferably, in formulas I and II, above, $R_2$ is hydrogen and $R_3$ is methyl, or $R_2$ together with $R_3$ form a trimethylene radical. $R_4$ and $R_5$ are preferably straightchain or branched alkyl radicals with 1–6 carbon atoms; most preferably, each is a methyl radical.

Preferably, in formulas I and III, above, $R_1$ is alkyl with 1 to 10 carbon atoms, cycloalkyl with 5 or 6 carbon atoms, norbonyl-(2)-methyl, benzoyl, phenylsulfonyl, phenyl and/or α-naphthyl. These radicals may preferably be substituted one or more times by alkyl of from 1 to 6 carbon atoms, chloroalkyl, bromoalkyl, fluoroalkyl having, in each case, 1 or 2 carbon atoms, chlorine, bromine, alkoxy of from 1 or 2 carbon atoms and/or phenyl.

The reaction may be effected in the presence of an inert organic solvent, and is generally effected at a temperature of 80° to 200°C.

It is very surprising that, according to the process of the invention, by heating the two components of the formulas (II) and (III) together the 2,3-dihydro-1,3-oxazinediones-(2,4) of the formula (I) may be obtained in good yields and high purity.

The process according to the invention, compared with the known methods, exhibits great advantages. Thus, the compounds of the general formula (I) can be prepared from readily accessible starting materials in a one-step process. Furthermore, it is advantageous that, according to the invention, only short reaction times, e.g., in the order of from 10 to 30 minutes, are generally necessary.

If, for example, 2,2,6-trimethyl-1,3-dioxinone-(4) and phenylisocyanate are used as starting materials, the reaction course can be represented by the following formula scheme:

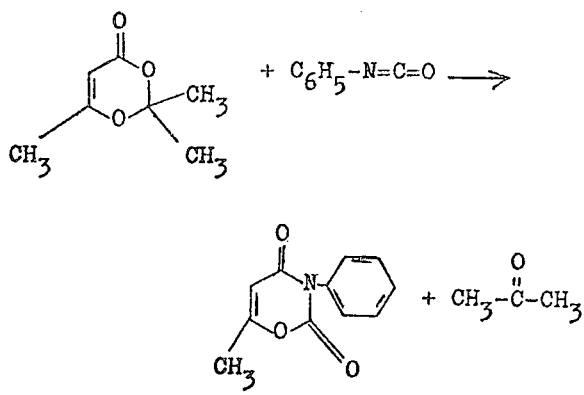

The 1,3-dioxinones-(4) to be used as starting materials are defined generally by the formula (II).

As examples of the 1,3-dioxinones-(4) which can be used according to the invention, there may be mentioned in particular:

2,2-dimethyl-4,5,6,7-tetrahydro-cyclopenta-1,3-dioxinone-(4),
2,2,7,7,-tetramethyl-4,5,6,7-tetrahydro-cyclopenta-1,3-dioxinone-(4),
2-ethyl-4,5,6,7-tetrahydro-cyclopenta-1,3-dioxinone-(4),
2,2-spiro-pentamethylene-4,5,6,7-tetrahydro-dioxinone-(4),
2-methyl-2-ethyl-4,5,6,7-tetrahydro-dioxinone-(4),
2-methyl-2-phenyl-4,5,6,7-tetrahydro-dioxinone-(4)
2-p-chlorophenyl-4,5,6,7-tetrahydro-dioxinone-(4)
2-phenyl-7,7-dimethyl-4,5,6,7-tetrahydro-dioxinone-(4)
2-phenyl-5,7,7-trimethyl-4,5,6,7-tetrahydro-dioxinone-(4)
2-(2-furyl)-4,5,6,7-tetrahydro-dioxinone-(4)
2-(β-styryl)-4,5,6,7-tetrahydro-dioxinone-(4)
2-(p-anisyl)-4,5,6,7-tetrahydro-dioxinone-(4)
2-(2-nitrophenyl)-4,5,6,7-tetrahydro-dioxinone-(4)
2-(4-tolyl)-4,5,6,7-tetrahydro-dioxinone-(4)

The 1,3-dioxinones-(4) used as starting materials are known. They can be prepared from diketenes and aldehydes or ketones in the presence of p-toluenesulfonic acid (cf. J. Am. Chem. Soc. 74, 6305 (1952) or by reaction of adipic acid dichlorides with aldehydes or ketones in the presence of an inert organic solvent at temperatures from −20° to +80°C. with the addition of a tertiary amine, for example triethylamine (see German Patent Application P 19 57 312.7 and Chemische Berichte, Volume 98, pages 2099 to 2102 (1965).

The isocyanates to be used as starting materials are defined generally by the formula (III).

The isocyanates are all known.

As examples of the isocyanates to be used according to the invention, there may be mentioned:

n-butylisocyanate, 6-chloro-n-hexylisocyanate, n-dicylisocyanate, benzylisocyanate, benzoylisocyanate, phenylisocyanate, α-naphthylisocyanate, 2,6-diisopropylphenylisocyanate, 3-difluoromethylphenylisocyanate 4-trifluoromethylisocyanate, 3-chloro-4-trifluoromethyl-phenylisocyanate, 4-chloro-3-trifluoromethyl-phenylisocyanate, 4-bromomethyl-phenylisocyanate, 4-anisylisocyanate, 4-ethoxyphenylisocyanate, [2,2,1]bicyclohept-2-yl-methylisocyanate, cyclohexylisocyanate, cyclopentylisocyanate, p-toluylsulfonylisocyanate, 2-phenylethylisocyanate and m-phenylenediisocyanate.

As stated above, the reaction of the invention may be effected in the presence of an inert organic solvent. A high-boiling inert organic solvent may be used. Such solvents include for example aliphatic and aromatic hydrocarbons, for example decalin, tetralin, toluene and xylene; halogenated hydrocarbons, for example chlorobenzene and 1,2-dichlorobenzene; nitroaromatics, for example nitrobenzene; and any desired mixtures of these solvents.

The reaction temperatures can be varied within a fairly wide range; in general, the reaction is carried out at a temperature from 80° to 200°C., preferably 120° to 170°C.

When carrying out the process according to the invention, the isocyanate and the 1,3-dioxinone-(4) are generally used in a molar ratio from 1 : 1 to 4 : 1, preferably 1.5 : 1. The 1,3-dioxinone-(4) as such, or a solution of the 1,3-dioxinone-(4) in one of the solvents mentioned above, may be added with stirring to the isocyanate as such, or to a solution of the isocyanate in one of the above-mentioned solvents, the isocyanate or solution thereof being heated to the appropriate temperature.

In the working up, either any excess isocyanate and, where appropriate, any solvent, may be distilled off under reduced pressure, or, in order to remove the isocyanate, the reaction mixture, after cooling, may be stirred with ether. The thus obtained compounds of formula (I) may be purified by the customary methods, for example by recrystallization.

Some of the compounds obtainable by the process of the invention are known (see in this connection J. Chem. Soc. 1954, 845 to 849 and Tetrahedron Letters 1967, 2089 to 2092).

A further feature of the present invention is that it provides new compounds which are of the formula (I) as defined above, with the proviso that, when $R_2$ is hydrogen and $R_3$ is methyl, $R_1$ is neither phenyl nor benzyl, and, when $R_2$ and $R_3$ form a trimethylene radical, $R_1$ is neither phenyl nor α-naphthyl.

The compounds of formula (I) can be used as intermediates for the preparation of crop protection agents. They can for example be converted by reaction with ammonia or an amine (See Examples A and B, below) into uracils which, as is known, possess a herbicidal effectiveness and can therefore be used for weed control destruction (see U.S. Pat. Nos. 3,235,360, 3,235,361 and 3,235,362 as well as Deutsche Auslegesschrift (German Published Specification) No. 1,240,698). The invention therefore provides uracils made by the above method.

The following Examples are illustrative of the invention.

EXAMPLE 1

Preparation of
3-(3-chloro-4-trifluoromethylphenyl)-6-methyl-2,3-dihydro-1,3-oxazinedione-(2,4)

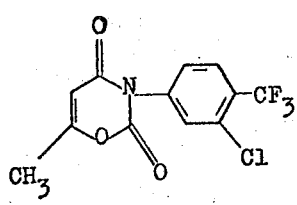    (1)

71 grams (0.5 mole) 2,2,6-trimethyl-1,3-dioxinone-(4) were added dropwise at 140°C., with stirring, to 165.75 grams (0.75 mole) 3-chloro-4-trifluoromethylphenylisocyanate, and the acetone formed was continuously distilled off. After completion of the addition, the excess isocyanate was distilled off in a high vacuum. After cooling, the distillation residue was stirred with either; filtration was effected, followed by recrystallization from methanol.

125 grams (82.5%) 3-(3-chloro-4-trifluoromethylphenyl)-6-methyl-2,3-dihydro-1,3-oxazinedione-(2,4) of the melting point 222° to 223° were obtained.

EXAMPLE 2

Preparation of
3-(4-chloro-3-difluoromethylphenyl)-6-methyl-2,3-dihydro-1,3-oxazinedione-(2,4)

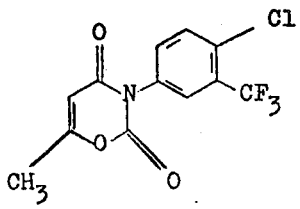    (2)

28.2 grams (0.2 mole) 2,2,6-trimethyl-1,3-dioxinone-(4) were added dropwise at 140°C., with stirring, to a solution of 60.8 grams (0.3 mole) 4-chloro-3-difluoromethylphenylisocyanate in 150 ml. dry xylene, and boiled under reflux for one hour. The solvent was distilled off in a water-jet vacuum, the excess isocyanate in a high vacuum; cooling was allowed to take place and the distillation residue was stirred with ether. Filtration was effected, followed by recrystallization from methanol, and 38.4 grams (67%) 3-(4-chloro-3-difluoromethylphenyl)-6-methyl-2,3-dihydro-1,3-oxazinedione-(2,4) of the m.p. 161° to 163°C. were obtained.

In manner analogous to that of Example 1, there may be prepared the compounds listed in the following Table 1. These compounds are of the general formula (I) in which $R_2$ is hydrogen and $R_3$ is methyl and the meaning of $R_1$ is set forth in the Table.

Table 1

| Example No. | $R_1$ | Melting point [°C] |
|---|---|---|
| 3 |  | 170 |
| 4 | naphthyl | 156 – 157 |
| 5 | 3-Cl-phenyl | 156 – 158 |
| 6 | 4-Cl-phenyl | 215 – 217 |
| 7 | 3,4-di-Cl-phenyl | 203 – 205 |
| 8 | 4-$CF_3$-phenyl | 231 – 232 |
| 9 | 3-$CHF_2$-phenyl | 99 – 100 |
| 10 | 4-$BrCH_2$-phenyl | 248 |
| 11 | 2,6-di-$CH(CH_3)_2$-phenyl | 197 – 199 |
| 12 | 2,6-di-$C_2H_5$-phenyl | 90 – 92 |
| 13 | 4-$CH_3O$-phenyl | 193 |
| 14 | 4-$C_2H_5O$-phenyl | 220 – 223 |
| 15 | $C_6H_5CH_2$– | 93 |

Table 1-continued

| Example No. | R₁ | Melting point [°C] |
|---|---|---|
| 16 | ⟨H⟩- (cyclohexyl) | 172 – 174 |
| 17 | (norbornyl)–CH₂– | 89 |

In manner analogous to that of Example 2, there may be prepared the compounds listed in the following Table 2. These compounds are also of formula (I) in which $R_2$ and $R_3$ are respectively hydrogen and methyl and $R_1$ has the meaning set forth in the Table.

Table 2

| Example No. | R₁ | Melting point [°C] |
|---|---|---|
| 18 | CH₃CH₂CH₂CH₂— | 63 |
| 19 | Cl—CH₂—(CH₂·)₄—CH₂— | 45 |
| 20 | Cl—CH₂—CH₂— | 100 – 102 |

EXAMPLE 21

Preparation of 3-phenyl-2,3,4,5,6,7-hexahydrocyclopenta[e]-1,3-oxazinedione-(2,4)

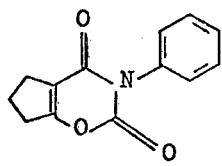 (21)

Variant (a)

A mixture of 33.6 grams (0.2 mole) 2,2-dimethyl-4,5,6,7-tetrahydrocyclopenta-1,3-dioxinone-(4) and 23.8 grams (0.2 mole) phenylisocyanate was heated rapidly to 140°C. and kept at this temperature for 10 minutes. The acetone formed in the reaction was continuously distilled off. After cooling to room temperature, the reaction mixture was stirred with 100 ml. of dry ether, and the reaction product which had crystallized out (and was sparingly soluble in ether) was filtered off with suction. After recrystallization from ethyl acetate with the addition of a little activated charcoal, 28 grams 3-phenyl-2,3,4,5,6,7-hexahydrocyclopenta[e]-1,3-oxazinedione-(2,4) of the melting point 145° to 146°C. were obtained.

Yield: 61% of the theory.

Variant (b)

Analogously with Variant (a), from 16.8 grams (0.1 mole) 2-ethyl-4,5,6,7-tetrahydrocyclopenta-1,3-dioxinone-(4) and 11 grams (0.1 mole) phenylisocyanate there were obtained 15.5 grams of the product of the melting point 145° to 146°C.

Yield: 67.5% of the theory.

EXAMPLE 22

Preparation of 3-[norbornyl-(2)-methyl]-2,3,4,5,6,7-hexahydrocyclopenta[e]-1,3-oxazinedione-(2,4)

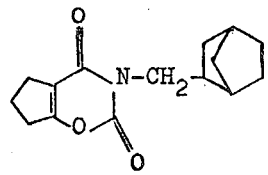 (22)

A solution of 16.8 grams (0.1 mole) 2,2-dimethyl-4,5,6,7-tetrahydrocyclopenta-1,3-dioxinone-(4) in 22.6 grams (0.15 mole) norbornyl-(2)-methylisocyanate was heated to 140°C. for 15 minutes. Excess isocyanate and low boiling impurities were distilled from the reaction mixture in a high vacuum at a bath temperature of 80°C. The liquid residue was dissolved in a little chloroform, the solution was put on a column charged with silica gel/chloroform and eluted with chloroform. The eluate was evaporated in a vacuum and solvent residues were removed in a high vacuum. 21 grams 3-[norbornyl-(2)-methyl]-2,3,4,5,6,7-hexahydrocyclopenta[e]-1,3-oxazinedione-(2,4) were obtained as colorless oil.

Yield: 80.5% of the theory.

| Analysis: | C | H | N |
|---|---|---|---|
| Calculated | 68.95% | 7.33% | 5.37% |
| Found | 68.51% | 7.06% | 5.23% |

IR-spectrum: Absorption at 1750 and 1690 cm⁻¹.

Analogously with Examples 21 (Method A in Table 3, below) and 22 (Method B in Table 3, below) the compounds contained in the following Table 3 can be prepared. These compounds are of the following general formula

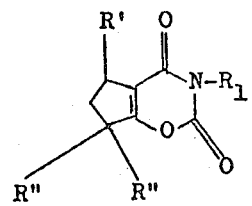

The meanings of $R_1$, R' and R'' are shown in the Table.

Table 3

| Example No. | R₁ | R¹ | R'' | Method | Physical properties |
|---|---|---|---|---|---|
| 23 |  (2-chlorophenyl) | H | H | A | m.p. 138–139°C |

Table 3-continued
| Example No. | R₁ | R¹ | R'' | Method | Physical properties |
|---|---|---|---|---|---|
| 24 |  | H | H | A | m.p. 155–156°C |
| 25 |  | H | H | A | m.p. 139–140°C |
| 26 |  | H | CH₃ | A | m.p. 167–169°C |
| 27 |  | CH₃ | CH₃ | A | m.p. 159–160°C |
| 28 | 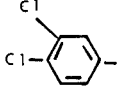 | H | H | A | m.p. 190–191°C |
| 29 | 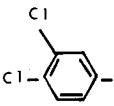 | H | CH₃ | A | m.p. 174–175°C |
| 30 | 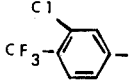 | H | H | A | m.p. 169–170°C |
| 31 | 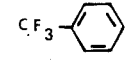 | H | H | A | m.p. 211–212°C |
| 32 |  | H | H | A | m.p. 197–198°C |
| 33 |  | H | H | A | m.p. 103.5–105°C |
| 34 | 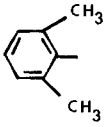 | H | H | A | m.p. 123–125°C |

Table 3-continued

| Example No. | R₁ | R' | R'' | Method | Physical properties |
|---|---|---|---|---|---|
| 35 | 2,6-di(isopropyl)phenyl [CH(CH₃)₂ groups on benzene ring] | H | H | A | m.p. 151–152°C |
| 36 | 2,6-di(ethyl)phenyl [C₂H₅ groups on benzene ring] | H | H | A | m.p. 135–136°C |
| 37 | CH₃O—C₆H₄— | H | H | A | m.p. 180–181°C |
| 38 | C₂H₅O—C₆H₄— | H | H | A | m.p. 214–216°C |
| 39 | C₂H₅O—C₆H₄— | H | CH₃ | A | m.p. 155–157°C |
| 40 | 1-naphthyl | H | H | A | m.p. 187–188°C |
| 41 | C₆H₅—CH₂—CH₂— | H | H | A | m.p. 115–116°C |
| 42 | cyclohexyl | H | H | A | m.p. 65–68°C |
| 43 | C₆H₅—C(=O)— | H | H | A | m.p. 143–145°C |
| 44 | CH₃—C₆H₄—SO₂— | H | H | A | m.p. 122–123°C |
| 45 | CH₃—CH₂—CH₂—CH₂— | H | H | B | $n_D^{24} = 1.5042$ |
| 46 | Cl—CH₂—CH₂—H | H | B | | $n_D^{24} = 1.5324$ |
| 47 | Cl—CH₂—(CH₂)₄—CH₂— | H | H | B | IR-spectrum: Absorption at 1750 μ. 1690 cm⁻¹. |

Table 3-continued

| Example No. | $R_1$ | $R'$ | $R''$ | Method | Physical properties |
|---|---|---|---|---|---|
| 48 | 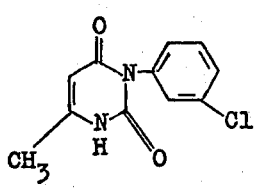 | H | H | A | m.p. 125.5–126.5°C |
| 49 | 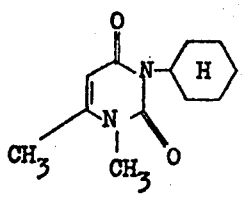 | H | H | A | m.p. 153.5–154.5°C |
| 50 | | H | H | A | m.p. 172.5–173.5°C |

EXAMPLE A

Reaction of 2,3-dihydro-1,3-oxazinedione-(2,4) according to Example 5 with ammonia with formation of the corresponding uracil An ammonia stream was introduced for 4 hours at 40°C. into a mixture of 30 grams 3-(3-chlorophenyl)-6-methyl-2,3-dihydro-1,3-oxazindione-(2,4) (Example 5) and 2 liters of 27%-strength aqueous ammonia solution. The reaction product which crystalized out was filtered off with suction and dried. 7 grams (23.5% of the theory) 3-(3'-chlorophenyl)-6-methyl-uracil of the melting point 250°–252°C. were obtained.

EXAMPLE B

Reaction of 2,3-dihydro-1,3-oxazinedione-(2,4) according to Example 16 with methylamine with formation of the corresponding uracil 20.9 grams (0.1 mole) 3-cyclohexyl-6-methyl-2,3-dihydro-1,3-oxazinedione-2,4-(Example 16) were introduced into 250 ml of 30% strength aqueous methylamine solution and allowed to stand for 14 hours at room temperature. The reaction product crystallized out, was filtered off and dried. 15 grams (64% of the theory) 1,6-dimethyl-3-cyclohexyluracil of the melting point 135° to 137°C. were obtained.

It will be understood that the specification and examples are illustrative but not limitative of the present invention and that other embodiments within the spirit and scope of the invention will suggest themselves to those skilled in the art.

What is claimed is:

1. Process for the production of a 2,3-dihydro-1,3-oxazinedione-(2,4) compound of the formula

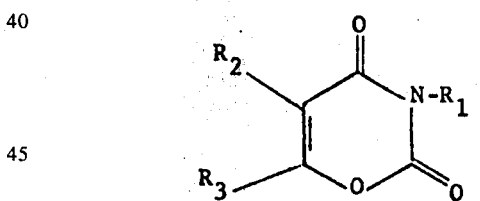

in which
$R_1$ is alkyl with 1 to 10 carbon atoms or cycloalkyl of from 5 to 6 carbon atoms, norbornyl methyl, benzyl, phenylethyl, benzoyl, phenylsulfonyl, phenylmercaptocarbonyl, phenyl or naphthyl which radicals may be substituted by up to three alkyl of from 1 to 6 carbon atoms, phenyl, alkoxy of from 1 to 2 carbon atoms, haloalkyl of from 1 to 2 carbon atoms, fluorine, chlorine, bromine, iodine, cyano, nitro, or amino groups; or $R_1$ can be trichloropyrimidyl or dichlorotriazyl; or $R_1$ can be the group of the formula

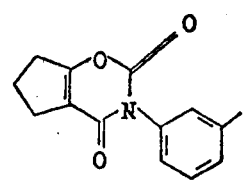

$R_2$ is hydrogen and $R_3$ is methyl, or $R_2$ and $R_3$ together form a trimethylene radical which may be substituted by one or more alkyl radicals,
which process comprises reacting, at a temperature of from 80° to 200°C, a 1,3-dioxinone-(4) of the formula

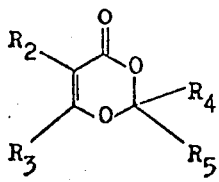

in which
$R_2$ and $R_3$ have the meaning stated above, and
$R_4$ is hydrogen or alkyl, and
$R_5$ is alkyl or aryl, or
$R_4$ and $R_5$ taken together form a divalent alkylene group of the formula $—(CH_2)_n—$, where $n$ is 4, 5 or 6;
with an isocyanate of the formula
$R_1'—N=C=O$
in which
$R_1'$ has the meaning stated above for $R_1$, except that $R_1'$ cannot be the group of the formula

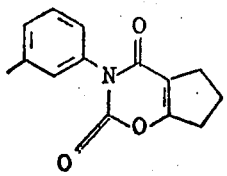

but $R_1'$ may also be a radical of the formula

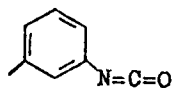

2. Process as claimed in claim 1 wherein $R_2$ is hydrogen and $R_3$ is methyl.

3. Process as claimed in claim 1 wherein $R_2$ and $R_3$ are taken together to form a trimethylene radical.

4. Process as claimed in claim 1 wherein $R_4$ and $R_5$ are each alkyl of from 1 to 6 carbon atoms.

5. Process as claimed in claim 1 wherein $R_1$ and $R_1'$ are alkyl of from 1 to 10 carbon atoms.

6. Process as claimed in claim 1 wherein $R_1$ and $R_1'$ are cycloalkyl of from 5 to 6 carbon atoms or norbornyl-2-methyl.

7. Process as claimed in claim 1 wherein $R_1$ and $R_1'$ are benzoyl.

8. Process as claimed in claim 1 wherein $R_1$ and $R_1'$ are phenyl or naphthyl.

9. Process as claimed in claim 1 wherein $R_1$ and $R_1'$ are phenylsulfonyl.

10. Process as claimed in claim 1 wherein $R_1$ and $R_1'$ are alkyl of from 1 to 10 carbon atoms, cycloalkyl of from 5 to 6 carbon atoms, norbornyl-2-methyl, benzoyl, phenyl, naphthyl or phenylsulfonyl and each of these radicals is substituted with at least one member of the group consisting of alkyl of from 1 to 6 carbon atoms, chloroalkyl, bromoalkyl, fluoroalkyl having, in each case, 1 or 2 carbon atoms, chlorine, bromine, alkoxy of from 1 or 2 carbon atoms and phenyl.

11. Process as claimed in claim 1 wherein the reaction is effected at approximately atmospheric pressure.

12. Process as claimed in claim 1 wherein the reaction is effected in the presence of an inert organic solvent.

13. Process as claimed in claim 1 wherein said isocyanate compound and said dioxinone compound are used in a molar ratio of about 1 : 1 to about 4 : 1.

14. Process as claimed in claim 1 wherein 3-(3-chloro-4-trifluoromethylphenyl)-6-methyl-2,3-dihydro-1,3-oxazinedione-(2,4) is produced by reacting 2,2,6-trimethyl-1,3-dioxinone-(4) with 3-chloro-4-trifluoromethylphenylisocyanate.

15. Process as claimed in claim 1 wherein 3-(4-chloro-3-difluoromethylphenyl)-6-methyl-2,3-dihydro-1,3-oxazinedione-(2,4) is prepared by reacting 2,2,6-trimethyl-1,3-dioxinone-(4) with 4-chloro-3-difluoromethylphenylisocyanate.

16. Process as claimed in claim 1 wherein 3-phenyl-2,3,4,5,6,7-hexahydrocyclopenta[e]-1,3-oxazinedione-(2,4) is prepared by reacting 2,2-dimethyl-4,5,6,7-tetrahydrocyclopenta-1,3-dioxinone-(4) with phenylisocyanate.

17. Process as claimed in claim 1 wherein 3-[norbornyl-(2)-methyl]-2,3,4,5,6,7-hexahydrocyclopenta[e]-1,3-oxazinedione-(2,4) is prepared by reacting 2,2-dimethyl-4,5,6,7-tetrahydrocyclopenta-1,3-dioxinone-(4) with norbornyl-(2)-methylisocyanate.

* * * * *

UNITED STATES PATENT AND TRADEMARK OFFICE
CERTIFICATE OF CORRECTION

PATENT NO. : 3,931,171
DATED : January 6, 1976
INVENTOR(S) : GERHARD JÄGER ET AL It is certified that error appears in the above—identified patent and that said Letters Patent are hereby corrected as shown below:

Page 1, item [75] "Inventors", correct spelling of second inventor -- Wenzelburger --.

Signed and Sealed this twenty-second Day of June 1976

[SEAL]

Attest:

RUTH C. MASON
*Attesting Officer*

C. MARSHALL DANN
*Commissioner of Patents and Trademarks*